United States Patent [19]
Capaccioli et al.

[11] Patent Number: 5,872,106
[45] Date of Patent: Feb. 16, 1999

[54] ANTIMESSENGER OLIGONUCLEOTIDE AGAINST UROKINASE RECEPTOR

[75] Inventors: Sergio Capaccioli; Mario Del Rosso; Gabriella Fibbi; Alessandro Quattroni, all of Florence, Italy

[73] Assignee: Consiglio Nazionale Delle Ricerche, Rome, Italy

[21] Appl. No.: 776,062

[22] PCT Filed: Jul. 17, 1995

[86] PCT No.: PCT/EP95/02793

§ 371 Date: Feb. 27, 1997

§ 102(e) Date: Feb. 27, 1997

[87] PCT Pub. No.: WO96/03414

PCT Pub. Date: Feb. 8, 1996

[30] Foreign Application Priority Data

Jul. 22, 1994 [IT] Italy ................................ MI94A1560

[51] Int. Cl.$^6$ ............................. C12Q 1/68; C12N 15/85; C07H 21/04; A61K 48/00
[52] U.S. Cl. ................................ 514/44; 435/6; 435/91.1; 435/172.3; 435/366; 435/375; 536/23.1; 536/24.31; 536/24.5; 514/44
[58] Field of Search ........................... 435/6, 91.1, 172.3, 435/366, 375; 536/23.1, 24.31, 24.5; 424/450; 514/44

[56] References Cited

FOREIGN PATENT DOCUMENTS 90 12091  10/1990  WIPO .

OTHER PUBLICATIONS

Cancer Research, vol. 50, pp. 7623–7633, 1 Dec. 1990, "Relationship between Secreted Urokinase Plasminogen Activator Activity and Metastatic Potential in Murine B16 Cells etc.", H. Yu et al.

The EMBO Journal, vol. 9, No. 2, Feb. 1990, Oxford, UK, pp. 467–474, "Cloning and expression of the receptor for human urokinase plasminogen activator, a central molecule etc.", A.L. Roldan et al.

Anti–cancer Drug Design, vol. 10, No. 1, Jan. 1995, Oxford, UK, pp. 97–102, "Antimessenger oligonucleotide for urokinase receptor gene inhibits invasivity of transformed etc.", A. Quattrone et al.

Rojanasakul, Antisense Oligonucleotide Therapeutics: Drug Delivery and Targeting, Advanced Drug Delivery Reviews 18, 115–131 (Jan. 15, 1996), (Dispatched Jan. 30, 1996).

*Primary Examiner*—John L. LeGuyader
*Assistant Examiner*—Mark L. Shibuya
*Attorney, Agent, or Firm*—Griffin, Butler, Whisenhunt & Szipl, LLP

[57] ABSTRACT

Antisense oligonucleotides optionally stabilized with phosphorotioate residues or analogues, or modified in the whole sugar-phosphate backbone—complementary to the human urokinase receptor messenger RNA—are able to prevent invasiveness of neoplastic cells by inhibiting the overexpression of the receptor itself, directly responsible of the invasive phenotype. Said oligomers are useful as medicaments for the treatment of primary and secondary neoplasias as well as of other pathologies wherein the urokinase receptor gene overexpression is a pathogenic event.

4 Claims, 2 Drawing Sheets

ANTIMESSENGER OLIGONUCLEOTIDE AGAINST UROKINASE RECEPTOR

This is a 371 of PCT/EP95/02793, filed Jul. 17, 1995.

BACKGROUND OF THE INVENTION

The present invention relates to antisense oligonucleotides complementary to mRNA of urokinase human receptor and to pharmaceutical compositions containing them as the active ingredients.

Plasminogen activation is considered a central process in the regulation of pericellular proteolysis which occurs under both normal and pathological conditions, including cancer invasion, when tissue destruction and cell migration are required. Even though the roles of tissue-type plasminogen activator (t-PA) and urokinase-type plasminogen activator (u-PA) in in vivo neoplasias and in vitro transformed cells have not yet been elucidated, however, it is now well established that u-PA plays a paramount role in neoplastic cell transformation (Physiol. rev. 73(1): 161–195, 1993).

After secretion as a zymogen (pro-u-PA), the active form is obtained by cleavage at lysine 158 into two chains connected by a disulfide bridge. As a result of their interaction with a specific receptor (u-PAR) (Advances in Cancer Res. 57:273–328, 1991) which belongs to the glycosyl-phosphatidyl inositol-anchored proteins family (Exp. Cell. Res. 203:427–434, 1992), pro-u-PA and the active enzyme equilibrate between solution and the cell surface. (Pro)-u-PA binds to the receptor by a sequence framed within the amino-terminal fragment of the A chain thus exposing the B chain, which contains the catalytic site, to the extracellular milieu. On some cell lines, growing as monolayers in vitro, urokinase receptors are located at specific sites on the ventral side of the cell: the so-called focal contacts. Other components of the plasminogen activation system have been identified on the extra-cellular side of cell contacts and have been suggested to play a regulatory role in the modulation of cell-substratum adhesion and extra-cellular matrix destruction. In particular, the presence of u-PA at the main contact sites of the cell has been considered critical in determining the detachment of the cell from the substratum and progression within tissues. Using cell monolayers, it has been observed that the adhesion sites specifically concentrate u-Pa binding sites (Advances in Cancer Res. 57:273–328, 1991).

A number of evidences exist that the expression of urokinase receptor is a basical factor of the invasive characteristics of tumour cells. It has particularly been suggested that the contribution of u-PAR to the invasive phenotype may involve the increased plasmin production by receptor-bound u-PA (J. Biol. Chem. 266: 752–758, 1991). Some authors (Cancer Res. 53:3139–3117, 1993) reported that the overexpression of an exogenous cDNA coding for the u-PA binding site in a human osteosarcoma cell line induced the increase of cell migration in the matrigel test, in addition to increased laminin degradation. In another study (Proc. Natle. Acad, Sci. USA 90:5021–5025, 1993), it was shown that displacement of receptor bound u-PA by a mutant u-PA lacking enzymatic activity, caused the reduction of brain, lung and regional lymph nodes metastasis of prostate cancer cells PC-3. Still other authors (Br. J. Cancer 67:537–544, 1993) have shown that the matrigel invasion by the ovarian cancer cell lines HOC-1 was inhibited by peptides corresponding to the u-PA receptor binding fragment.

It is therefore evident that the u-PA/u-PAR system may be a target for drugs which, decreasing or blocking the invasive action of the cells, may be useful as anti-tumor and anti-metastatic agents.

It has been already shown, for instance, that antibodies against human u-PA prevent the metastasis formation in chicken embryonal lung of human carcinoma cells (Cell 35:611–619, 1983). The anti-messenger strategy has also been used against the u-PA gene in NIH 3T3 cells: in such a case, the selective block of the u-PA gene induced in the cells an alternative invasive mechanism based on the gene expression of another protease, cathepsin L (Cancer Res. 52:6682–6689, 1992).

SUMMARY OF THE INVENTION

It has now been found that antisense oligonucleotides complementary to messenger RNA sequences of human urokinase receptor are able to inhibit the invasiveness of SV-40 transformed human fibroblasts (VA 13 cells). Said transformed cells expose u-PA receptors (u-PAR) to an extent 10 times higher compared to normal cells (WI-38 cells).

The antisense oligonucleotides according to the invention typically comprise from about 10 to about 50 nucleodites and more preferably from 12 to 30 nucleotides. The minimal length of the oligonucleotides sequence is obviously determined by the hybridization specificity to the target sequence whereas the maximum length must of course take into consideration the penetration capability through the cell membranes.

The oligonucleotides of the invention preferably have a sequence able to hybridise to the messenger RNA of human u-PAR in correspondence to the translation starting site. With reference to the human u-PAR cDNA sequence published in EMBO J. 9(2):467–474, 1990, said translation starting site is found at the 44–61 residues. It is therefore particularly preferred the oligonucleotide having the following sequence (Sequence Id No. 1:

5'-CGG CGG GTG ACC CAT GTC-3'.

DESCRIPTION OF THE PREFERRED EMBODIMENTS

Figure 1:
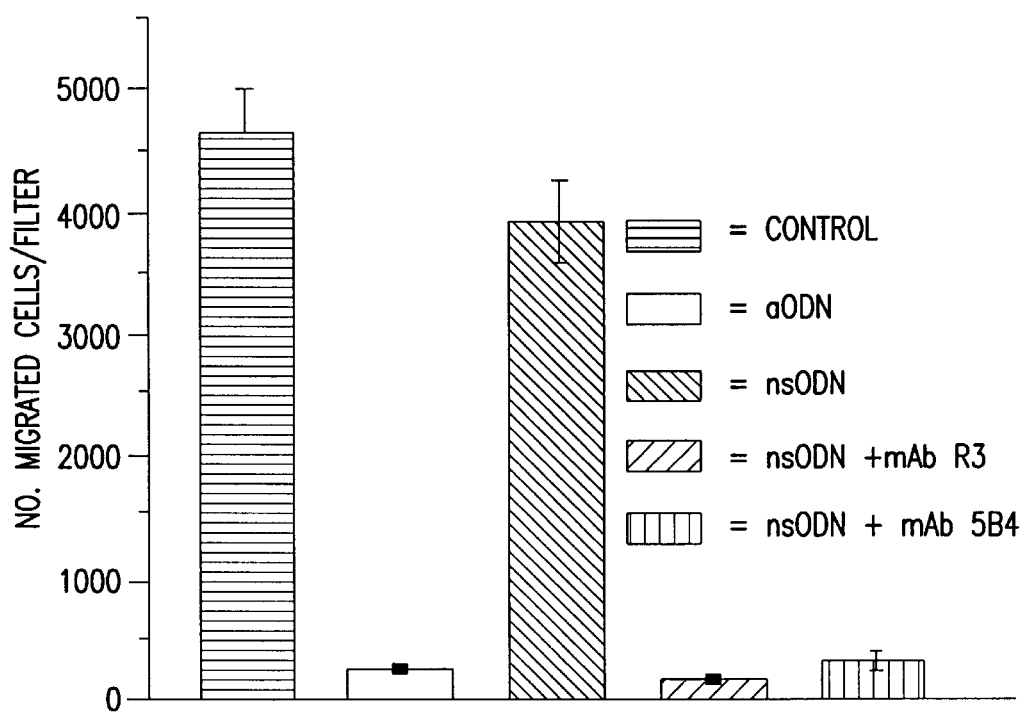
FIG. 1 is a graph which shows that treatment with an oligonucleotide of the invention resulted in a decrease in cell invasivity.

The oligonucleotides of the invention may be prepared according to known methods, as described for instance in Tetrahedron 39:3, 1983; Ann. Rev. Biochem. 53:323, 1984; "Oligonucleotide Synthesis; A practical Approach", Yait M. J. Ed. IRL Press., Oxford, U.K. 1984; Chem. Rev. 90(4) 543, 1990.

The oligonucleotides of the invention will also preferably be stabilized in order to improve the cell penetration and to prolong half-life, using conventional structural modifications, such as disclosed for instance in Chem. Rev. 90(4), 543, 1990.

These modifications mainly but not exclusively concern the internucleotidic phosphate bridge which may be transformed in a methylphosphonate, phosphorothioate or phosphorodithioate, phosphoroamidate groups, phosphate esters etc.

The derivatives completely substituted or substituted at the 3'- and 5'end with phosphorothioate residues are particularly preferred.

The oligonucleotides may also be covalently bound to a lipid, as diclosed for instance in WO 90/10448, so as to make the transport through the cell membranes easier to be then cleaved to the active oligonucleotides by cytoplasmatic enzymes.

For the intended therapeutic uses, particularly for the treatment of primary or secondary neoplastic diseases, as well as of other pathological forms wherein the overexpression of urokinase receptor is a pathogenetic event, the invention refers also to pharmaceutical compositions containing the antisense oligonucleotides of the invention in admixture with carrier suited for the oral or parenteral administration. The compositions of the invention, prepared according to conventional methods such as disclosed for instance in "Remington's Pharmaceutical Sciences Handbook", Mack Pub. Co., NY, USA, XVII Ed., will contain from 0.1 to 100 mg of the oligonucleotide and they will be generally administered from 1 to 4 times a day, according to the physician's prescription. According to a particularly preferred embodiment, the oligonucleotides are formulated in liposomial form, particularly in cationic liposomial form, using DOTAP (Boehringer Mannheim) according to known methods (Biochem. Biophys. Res. Commun. 107:818–825, 1993). The invention will now be described more in detail in the following examples.

EXAMPLE 1

An oligonucleotide having the following sequence (Sequence ID No. 1):

5'-CGG CGG GTG ACC CAT GTC-3' was synthesized by means of a DNA synthesizer.

This nucleotide was substituted with phosphorothioate residues at the 3'- and 5'-end, according to known methods. The obtained oligonucleotides, purified by HPLC, was pre-incubated at 37° C. for 35' in the presence of DOTAP, sterilized thorugh a 0.2 µM filter and applied to the culture medium containing 10% heat-inactivated FCS (Gibco, USA) at final concentrations of 10 µM of oligonucleotide and 13 µM of DOTAP.

EXAMPLE 2

Treatment of cell monolaver with oliconucleotides

The cell lines WI-38 (human embryonic lung fibroblasts) and VA-13 cells, obtained from the cell line WI-38 by transformation with the virus SV 40 were used. Said cells are commercially available from Flow Laboratories (Milano, Italy), and cultured in Dulbecco's modified medium supplemented with 10% fetal calf serum, in an atmosphere of 5% $CO_2$-95% air at 37° C. The transformed VA-13 cells, characterized by the overexpression of u-PAR and the WI-38 normal cells were seeded at $20 \times 10^3$ cells/well in 24-well Petri dish in DMEM containing 10% heat-inactivated FCS. The oligonucleotide/DOTAP complex of example 1 was added to the culture medium at a concentration of 10 µM and the dishes were incubated at 37° C. for 4 days. To keep the oligonucleotide concentration constant, a second addition of the oligonucleotide/DOTAP complex of example 1 was performed 48 hours later, at a concentration of 5 µM.

Aliquots of the medium of both cell lines, grown to confluence in 25 cc Falcon flasks, were used directly in cross-linking experiments. Cell monolayers were washed twice with PBS and subjected to acid washing to uncouple endogenous u-PA from the receptor. After neutralization and further washing in PBS, cells were lysed in the flasks with 500 µl lysis buffer (0.5% CHAPS, 0.1M Tris-HCl pH 8.0, 10 mM EDTA, 1% aprotinin, 1% Triton X 114, 1 mM phenylmethane-sulfonyl fluoride [PMSF] and the mixture was centrifuged. In parallel cultures, cells were detached with 500 pl EDTA in PBS and centrifuged. The pellet was lysed in 500 µl lysis buffer and an aliquot was used for cross-linking. The material eventually remaining on the flask after EDTA detachment (SAM, surface attached material) was washed 5 times with 10 ml PBS and extracted with 500 µl lysis buffer and an aliquot was subjected to cross-linking, using radiolabelled ATF (amino terminal residue of 140 amino acids of human u-PA). 50 µl of each sample were incubated with $500 \times 10^3$ cpm of 125 I-ATF with or without 100 mM unlabelled u-PA for 60 min at 4° C., then N,N'-disuccinimidyl suberate (final concentration 1 mM) was added, the mixture was incubated at room temperature for 15 min. and cross-linking was stopped by addition of ammonium acetate to 10 mM. The samples were then analyzed by SDS-PAGE under non reducing conditions and autoradiography.

The obtained results prove that the 4 day-exposure of VA-13 cells to a 10 µm concentration of antisense oligonucleotide caused a remarkable decrease in u-PAR at the cell surface. Competition-binding experiments performed on acidified VA-13 monolayers indicated a remarkable decrease of u-PAR following a treatment with the oligonucleotide: 37.5 ($\pm 6.3$)$\times 103$ receptors/cell.

The oligonucleotide-treated cells were subjected to the invasion assay to evaluate their ability to penetrate the basement membrane Matrigel, in the presence of the WI-38 conditioned medium in the lower compartment of the migration chamber. The basement membrane Matrigel, an extract of the the Englebreth-Holm-Swarm tumour, commercially available from Collaborative Research, was used as a stock solution with a protein concentration of 10 mg/ml. Blind well chemotaxis chambers with 13-mm diameter filters were used for the invasion assay. Polyvinylpyrrolidone-free polycarbonate filters, 8 µm pore size (Nuclepore, Calif.), were coated with 50 µg/filter of matrigel. The matrigel was diluted to the final concentration with cold distilled water, applied to the filters, dried under a hood, and reconstituted with serum-free medium. The coated filters were placed into Boyden chambers. Cells ($40 \times 10^3$), suspended in serum-free DMEM, were added to the upper chamber. Conditioned medium (obtained from WI-38 human fibroblasts maintained in, culture in serum-free conditions for 24 h after confluence) was placed into the lower compartment of the Boyden chamber. This medium was used as a source of chemoattractants. Alternatively, u-PA was placed into the lower compartment of the migration chamber. Cell migration in the absence of chemoattractants (DMEM alone) in the lower compartment, was taken as background migration for each cell line over a 5 hours period. Cell migration could not be attributed to passive diffusion since the pore size of the filters is smaller than the cells. In some experiments, cells in the upper compartment of the migration chamber were incubated with monoclonal antibodies in order to obtain an immunosuppression of the invasive process. Assays were carried out at 37° C. in 5% $Co_2$ for 5 hours. At the end of incubation filters were removed and fixed in methanol for 2 hours. The cells on the upper part of the filters were then completely removed by wiping with a rubber swab. The filters were stained with fucsin and all the cells attached to the lower surface, that is the invasive cells, were counted. Each assay was performed in quadruplicate.

These conditions revealed the highest differences between normal and transformed cells, either in the absence or in the presence of monoclonal antibodies (mAb R3 and mAb 5B4) in the upper compartment of the invasion system. FIG. 1 shows that the oligonucleotide treatment resulted in a considerable decrease in cell invasivity. The number of cells on the underside of the migration filter resulted even lower than under conditions of spontaneous random migration, approaching that of WI-38 cells. As a control, a non-sense oligonucleotide (nsODN) having the same base composition as the anti-senge oligonucleotide (aODN) of example 1, but with a scrambled sequence.

Figure 2:
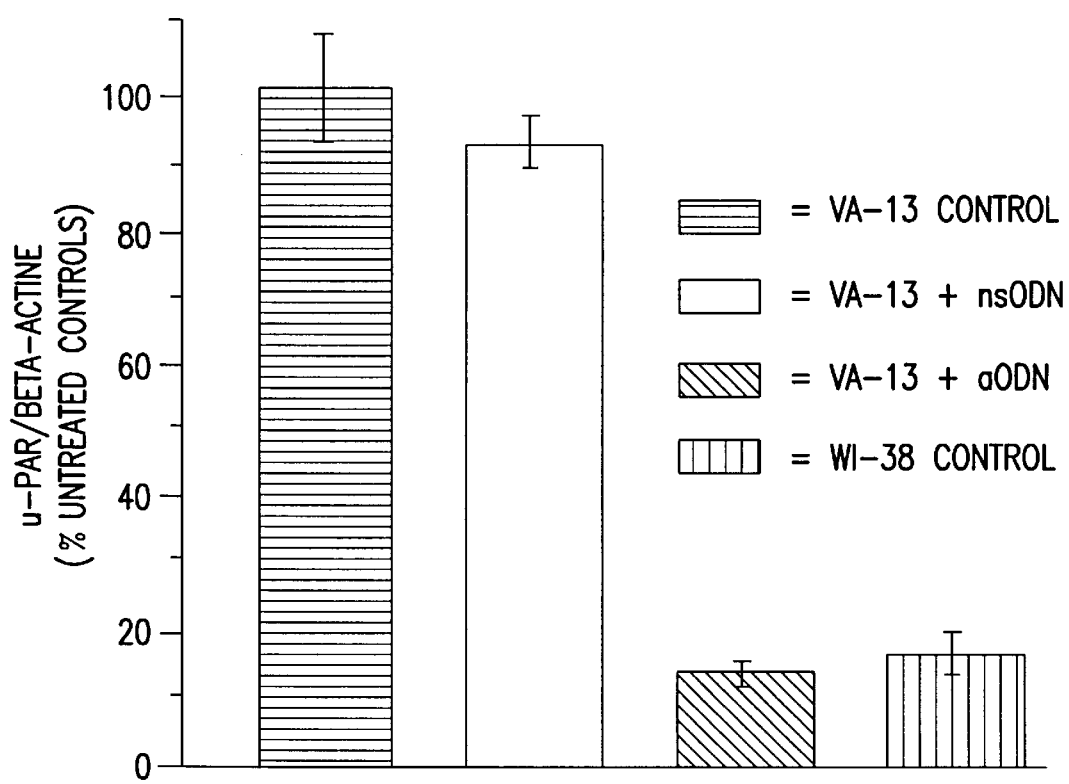
FIG. 2 is a graph which shows a decrease of u-PAR mRNA levels upon treatment with an oligonucleotide of the invention as compared with treatment with control oligonucleotides.

In order to verify that the loss of the invasive properties and the remarkable decrease in membrane u-PAR of the treated VA-13 cells is actually a consequence of the anti-messenger-mediated u-PAR gene expression inhibition, u-PAR mRNA levels of the VA-13 cells treated with the oligonucleotide of example 1 were measured. An internal standard-based quantitative RT-PCR assay was used (Cancer Res. 52, 108–116, 1992). As shown in FIG. 2, a 4-day exposure of VA-13 cells to 10 $\mu$M aODN vehiculated by 13 $\mu$M DOTAP resulted in a dramatic decrease (more than 80%) of u-PAR MRNA levels as compared with both the untreated and random-sequence oligonucleotide treated controls. Therefore, as evidenced by this assay, the final steady-state levels of u-PAR gene mRNA in the treated cells are similar to those of normal untreated WI-38 cells. This result indicates a complete reversion of u-PAR gene overexpression, as a consequence of the aODN administration.

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: YES ( x i ) SEQUENCE DESCRIPTION: SEQ ID NO: 1:

C G G C G G G T G A   C C C A T G T C         1 8

We claim:

1. An antisense oligonucleotide having the following sequence (Sequence ID No. 1):

5'-CGG CGG GTG ACC CAT GTC-3'.

2. A composition comprising the oligonucleotide of claim 1 and a carrier.

3. The composition of claim 2, wherein the carrier is a cationic liposomal form.

4. The composition of claim 3, wherein the cationic liposomal carrier is DOTAP.

* * * * *